US00PP16202P2

(12) United States Plant Patent
Radler

(10) Patent No.: US PP16,202 P2
(45) Date of Patent: Jan. 10, 2006

(54) SHRUB ROSE PLANT NAMED 'RADTKO'

(50) Latin Name: *Rosa hybrida*
Varietal Denomination: Radtko

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 100 days.

(21) Appl. No.: 10/873,196

(22) Filed: Jun. 23, 2004

(51) Int. Cl.
*A01H 5/00* (2006.01)

(52) U.S. Cl. ..... Plt./108

(58) Field of Classification Search ..... Plt./108, Plt./107, 150
See application file for complete search history.

*Primary Examiner*—Anne Marie Grunberg
*Assistant Examiner*—June Hwu
(74) *Attorney, Agent, or Firm*—Burns, Doane, Swecker & Mathis, LLP

(57) ABSTRACT

A new and distinct variety of landscape shrub rose plant is provided which forms in abundance on a substantially continuous basis attractive double blossoms that are red in coloration and possess significantly more petals than the 'Radrazz' variety (U.S. Plant Pat. No. 11,836). The vegetation is vigorous and the growth habit is round and bushy. Attractive ornamental satiny green foliage is formed. Excellent disease resistance to blackspot is exhibited as well as very good winter hardiness. The new variety is particularly well suited for growing as distinctive ornamentation in the landscape.

2 Drawing Sheets

Figure 1:
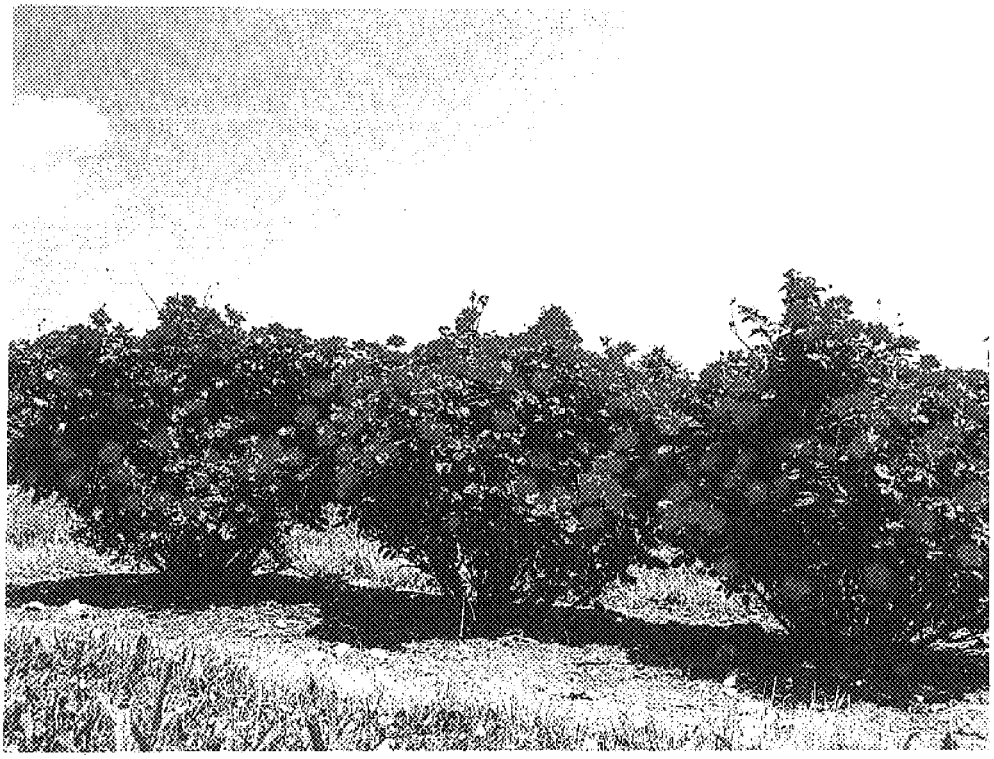

Botanical/commercial classification: *Rosa hybrida*/Shrub Rose Plant.
Varietal denomination: cv. Radtko.

SUMMARY OF THE INVENTION

The new variety of *Rosa hybrida* landscape shrub rose plant of the present invention was created by artificial pollination wherein two parents were crossed which previously had been studied in the hope that they would contribute the desired characteristics. The female parent (i.e., the seed parent) was a seedling of the 'Bucbi' variety (U.S. Plant Pat. No. 4,225). The 'Bucbi' variety is marketed under the CAREFREE BEAUTY trademark. The male parent (i.e., the pollen parent) of the new variety was a seedling of the 'Razzle Dazzle' variety (U.S. Plant Pat. No. 3,995). The parentage of the new variety can be summarized as follows:

'Bucbi' seedling×'Razzle Dazzle' seedling.

Such parental plants are the same as those used when creating the 'Radrazz' variety (U.S. Plant Pat. No. 11,836).

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) abundantly and substantially continuously forms attractive double blossoms that are red in coloration and possess significantly more petals than the 'Radrazz' variety (U.S. Plant Pat. No. 11,836), (b) exhibits a round and bushy growth habit, (c) forms vigorous vegetation, (d) forms attractive ornamental green foliage with a satiny finish, and (e) exhibits excellent resistance to blackspot.

The blooming cycle is believed to be one of the longest observed to date and is generally comparable to that of the 'Radrazz' variety. Also, the winter hardiness has been very good during observations to date.

The new variety well meets the needs of the horticultural industry. It can be grown to advantage as attractive ornamentation in parks, gardens, public areas, and in residential settings. It is particularly well suited for growing in the landscape. The bright red blossoms having an increased number of petals contrast nicely with the satiny green foliage.

The new variety of the present invention can be readily distinguished from the 'Radrazz' variety. More specifically, the blossoms of the new variety are double and display substantially more petals than the single blossoms of the 'Radrazz' variety. For example, the blossoms of the new variety commonly display approximately 23 petals on average while those of the 'Radrazz' variety and commonly display approximately 10 petals on average. The growth habit of the new variety tends to be slightly more compact and dense than that of the 'Radrazz' variety. Also, winter hardiness has been observed to be superior to that of the 'Radrazz' variety.

The new variety of the present invention also can be readily distinguished from its ancestors. More specifically, the new variety of the present invention forms deep red blossoms while those of the 'Bucbi' variety are pink, forms new foliage having flushes of deep burgundy which are lacking in the 'Bucbi' variety, and forms darker green mature foliage than the 'Bucbi' variety. The deep red blossom coloration of the new variety is present on both surfaces of the petals. The 'Razzle Dazzle' variety is a Floribunda that forms blossoms that are blood red on the inner surface and near white on the outer surface, and lacks flushes of deep burgundy on the new foliage.

The characteristics of the new variety have been found at Waso, Calif., U.S.A., to be homogeneous and stable and are strictly transmissible by asexual propagation such as budding, grafting, and the rooting of cuttings from one generation to another. The new variety reproduces true to type by such asexual propagation.

The new variety has been named the 'Radtko' variety.

BRIEF DESCRIPTION OF THE PHOTOGRAPHS

The accompanying photographs show, as nearly true as it is reasonably possible to make the same in color illustrations of this character, typical specimens of the new variety. The rose plants of the new variety illustrated herein were approximately five years of age and were observed during mid-May, 2004, while growing outdoors near West Grove, Pa., U.S.A. Such plants had undergone no spraying and were budded on 'Dr. Huey' understock.

Figure 2:
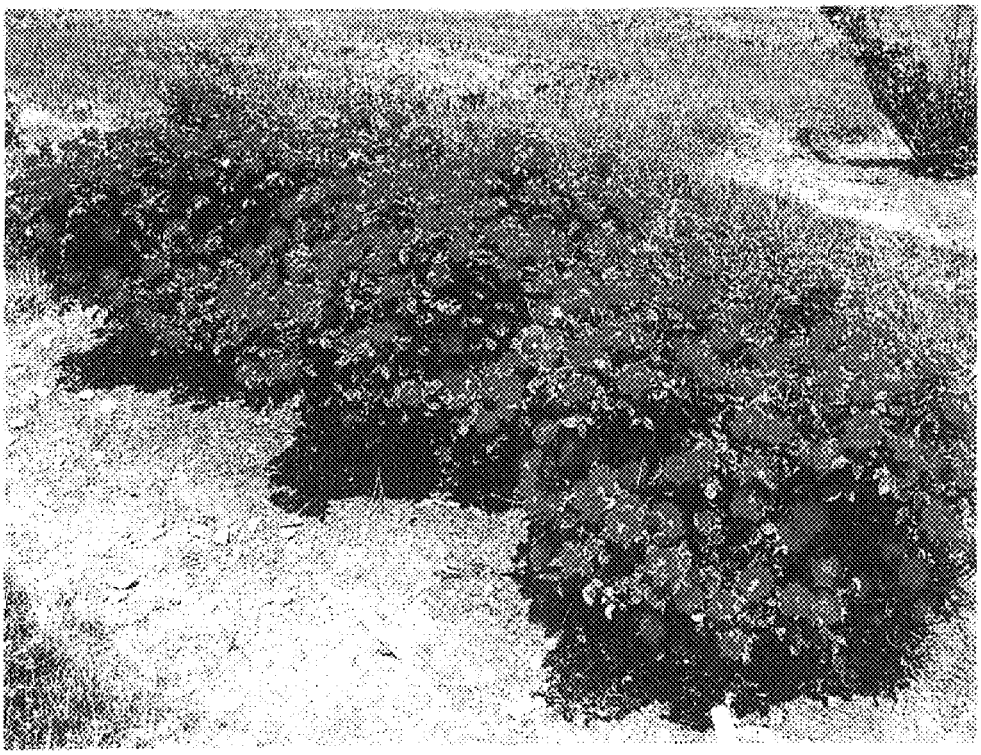

FIGS. 1 and 2 each illustrate a group of three specimens of the new variety while abundantly flowering. The attractive bright red double blossoms and the neat, dense and compact growth habit are shown.

DETAILED DESCRIPTION

The chart used in the identification of colors is that of The Royal Horticultural Society (R.H.S. Colour Chart), London, England. The description is based on the observation of two year-old specimens of the new variety during October while growing outdoors on their own roots near West Grove, Pa., U.S.A.

Class: Landscape Shrub Rose.

Plant:

*Height.*—Approximately one meter on average at the end of the growing season.

*Width.*—Approximately one meter on average at the end of the growing season.

*Habit.*—Round, and bushy.

Branches:

*Color.*—Young stems: near Yellow-Green Group 144B with some highlights of Red Group 53A. Adult wood: Yellow-Green Group 144B suffused with Greyed-Purple Group 184A.

*Texture.*—Stems bear a smooth surface texture when young and when mature.

*Thorns.*—Size: approximately 1 to 1.5 cm in length on average with some smaller bristles/prickles near the peduncle. Quantity: commonly approximately 18 per branch on average. Shape: oblong at the base and tapering to a fine point at the apex. Color: Greyed-Orange Group 176C when immature, and Greyed-Purple Group 184B when mature.

Leaves:

*Stipules.*—Approximately 15 mm in length, approximately 4 mm in width, parallel with the auricle facing outward, and Yellow-Green Group 144B in coloration.

*Petioles.*—Upper surface: Yellow-Green Group 144A with highlights of Greyed-Purple Group 184A and some prickles. Under surface: Yellow-Green Group 144B. Length: commonly approximately 24 mm on average. Rachis: commonly approximately 20 mm in length on average, and Yellow-Green Group 144B in coloration on the upper and under surfaces with a hint of Red Group 53A.

*Leaflets.*—Number: 3, 5, and 7. Shape: ovate with a serrulate margin, rounded base, and an acuminate tip. Margins: serrulate. Texture: smooth. Leaflet size: commonly approximately 5 cm in length and approximately 3.2 cm in width on average for a terminal leaflet, and approximately 3 cm in length and approximately 1.7 cm in width for other leaflets. Overall leaf size: commonly approximately 9.5 cm in length including the petiole and approximately 8 cm in width on average for a three-leaflet leaf, and approximately 12 cm in length including the petiole and approximately 8.7 cm in width on average for a five-leaflet leaf. Overall appearance: very dense, leathery, and medium green in coloration, with a satiny finish. Color (young foliage): upper surface: Greyed-Purple Group 187A with highlights of Green Group 141D. Under surface: Greyed-Purple Group 187B. Color (adult foliage): upper surface: commonly between Yellow-Green Group 147A and Green Group 137A. Under surface: Yellow-Green Group 147B with some Yellow-Green Group 148D.

Inflorescence:

*Number of flowers.*—Commonly approximately 4 or 5 blooms on average in a cluster.

*Peduncle.*—Medium green, Green Group 141D, with some prickles, approximately 6 cm in length on average, approximately 2.1 mm in diameter, and possesses superior strength with the flowers being held upright.

*Sepals.*—Upper surface: between Yellow-Green Group 144A and Yellow-Green Group 144B. Under surface: Yellow-Green Group 144B with areas of White Group 155D and some pubescence. Number: five. Size: approximately 27 mm in length on average and approximately 7 mm in width on average at the widest point. Margin: commonly bears some fine hairs at the edges. Apex: acuminate.

*Buds.*—Shape: slender. Length: approximately 2.5 cm on average. Size: small to medium. Color (when opening): upper surface: commonly between Red Group 52A and Red Group 55C. Under surface: commonly between Red Group 53C and Red Group 53D.

*Flower.*—Form: double and informal. Diameter: approximately 8 cm. on average. Color (when opening begins): upper surface: Crimson, near Red Group 52A. Under surface: between Red Group 52B and Red Group 53D. Color (when blooming): upper surface: Red Group 53D and Yellow Group 2C at the base. Under surface: Red Group 45A changing to near Yellow Group 2C at the center. Color (at end of blooming): upper surface: between Red Group 53D and Red Group 54A and near Yellow Group 4D at the base. Under surface: Red Group 55A with highlights of Red Group 55B and near Yellow Group 4D at the base. Fragrance: mild spice. Petal form: wedge-shaped with a curled apex. Petal size: commonly approximately 43 mm in length on average and approximately 35 mm in width on average. Petal number: approximately 23 on average. Petaloids: none observed. Lasting quality: blossoms commonly last approximately two weeks on the plant and approximately three weeks when cut and placed in a vase. Petal drop: very good, the petals drop cleanly and freely. Stamen number: approximately 113 on average. Anthers: approximately 3 mm in length on average, approximately 1.8 mm in width on average, and Yellow Group 11A in coloration. Filaments: approximately 6.3 mm in length on average, and Red Group 48D in coloration. Pistils: are separate and free, and number approximately 36 on average. Stigmas: approximately 0.75 mm in size on average, and Yellow Group 13C in coloration. Styles: approximately 5.5 mm in length on average, and Red Group 45B in coloration. Receptacle: smooth, generally rounded, approximately 13 mm in length, approximately 9 mm in width, Yellow-Green Group 144B in coloration, and with achenes standing on the bottom and wall.

Development:

*Vegetation.*—Vigorous and strong.

*Blossoming.*—Abundant and substantially continuous.

*Hardiness.*—Very good and believed to be somewhat superior to that of the 'Radrazz' variety. The new variety has successfully over-wintered at Greenfield, Wis., U.S.A.

*Resistance to diseases.*—Excellent with respect to blackspot and rust.

*Formation of hips/seeds.*—Sparse.

I claim:

1. A new and distinct variety of landscape shrub rose plant characterized by the following combination of characteristics:

(a) abundantly and substantially continuously forms attractive double blossoms that are red in coloration and possess significantly more petals than the 'Radrazz' variety (U.S. Plant Pat. No. 11,836), (b) exhibits a round and bushy growth habit, (c) forms vigorous vegetation, (d) forms attractive ornamental green foliage with a satiny finish, and (e) exhibits excellent resistance to blackspot;

substantially as herein shown and described.

* * * * *